(12) United States Patent
Brown

(10) Patent No.: US 6,595,945 B2
(45) Date of Patent: Jul. 22, 2003

(54) GLAUCOMA TREATMENT DEVICE AND METHOD

(76) Inventor: J. David Brown, 257 Mount Curve Blvd., St. Paul, MN (US) 55105-1211

( * ) Notice: Subject to any disclaimer, the term of this patent is extended or adjusted under 35 U.S.C. 154(b) by 0 days.

(21) Appl. No.: 09/757,502

(22) Filed: Jan. 9, 2001

(65) Prior Publication Data

US 2002/0169468 A1 Nov. 14, 2002

(51) Int. Cl.[7] ................................................ A61M 5/00

(52) U.S. Cl. .................................... 604/8; 604/9; 604/10; 604/48; 604/521; 604/289; 604/290

(58) Field of Search ........................ 604/8, 9, 10, 289, 604/290, 521, 48; 606/108

(56) References Cited

U.S. PATENT DOCUMENTS

| | | | |
|---|---|---|---|
| 3,159,161 A | 12/1964 | Ness | |
| 3,788,327 A | * 1/1974 | Donowitz et al. | 128/350 R |
| 4,402,681 A | 9/1983 | Haas et al. | |
| 4,521,210 A | 6/1985 | Wong | |
| 4,554,918 A | 11/1985 | White | |
| 4,604,087 A | 8/1986 | Joseph | |
| 4,634,418 A | 1/1987 | Binder | |
| 4,655,745 A | 4/1987 | Corbett | |
| 4,722,724 A | 2/1988 | Schocket | |
| 4,729,761 A | 3/1988 | White | |
| 4,750,901 A | 6/1988 | Molteno | |
| 4,758,237 A | * 7/1988 | Sacks | 604/294 |
| 4,787,885 A | 11/1988 | Binder | |
| 4,826,478 A | 5/1989 | Schocket | |
| 4,886,488 A | 12/1989 | White | |
| 4,936,825 A | 6/1990 | Ungerleider | |
| 4,946,436 A | 8/1990 | Smith | |
| 4,968,296 A | 11/1990 | Ritch et al. | |
| 5,041,081 A | 8/1991 | Odrich | |
| 5,071,408 A | 12/1991 | Ahmed | |
| 5,073,163 A | * 12/1991 | Lippman | 604/9 |
| 5,092,837 A | 3/1992 | Ritch et al. | |
| 5,171,213 A | 12/1992 | Price, Jr. | |
| 5,178,604 A | 1/1993 | Baerveldt et al. | |
| 5,300,020 A | 4/1994 | L'Esperance, Jr. | |
| 5,342,370 A | 8/1994 | Simon et al. | |
| 5,346,464 A | 9/1994 | Camras | |
| 5,360,399 A | * 11/1994 | Stegmann | 604/49 |
| 5,370,607 A | 12/1994 | Memmen | |
| 5,372,577 A | 12/1994 | Ungerleider | |
| 5,397,300 A | 3/1995 | Baerveldt et al. | |
| 5,433,701 A | 7/1995 | Rubinstein | |
| 5,454,796 A | 10/1995 | Krupin | |
| 5,476,445 A | 12/1995 | Baerveldt et al. | |
| 5,558,629 A | 9/1996 | Baerveldt et al. | |
| 5,573,544 A | 11/1996 | Simon et al. | |
| RE35,390 E | 12/1996 | Smith | |
| 5,626,558 A | 5/1997 | Suson | |
| 5,651,782 A | 7/1997 | Simon et al. | |
| 5,676,679 A | 10/1997 | Simon et al. | |
| 5,702,414 A | 12/1997 | Richter et al. | |

(List continued on next page.)

FOREIGN PATENT DOCUMENTS

| WO | WO 96/36377 | 11/1996 |
|---|---|---|
| WO | WO 99/26567 | 6/1999 |

Primary Examiner—Ira S. Lazarus
Assistant Examiner—Tu Cam Nguyen
(74) Attorney, Agent, or Firm—Fish & Richardson P.C.

(57) ABSTRACT

A device for treating glaucoma in an eye is described.

The device includes a body defining a lumen and having first and second ends and external and lumenal surfaces, wherein the body has a length sufficient to provide fluid communication between the anterior chamber and tear film of the eye through the lumen when the device is implanted in the sclera. The device further includes a filter capable of providing outflow resistance to aqueous humor flowing through the lumen. Methods of treating glaucoma wherein the device is implanted in the sclera of an afflicted eye are also described.

34 Claims, 6 Drawing Sheets

U.S. PATENT DOCUMENTS

| | | |
|---|---|---|
| 5,704,907 A | 1/1998 | Nordquist et al. |
| 5,725,493 A * | 3/1998 | Avery et al. .................... 604/9 |
| 5,743,868 A * | 4/1998 | Brown et al. ................... 604/8 |
| 5,752,928 A | 5/1998 | de Roulhac et al. |
| 5,785,674 A | 7/1998 | Mateen |
| 5,807,302 A | 9/1998 | Wandel |
| 5,868,697 A * | 2/1999 | Richter et al. ................. 604/8 |
| 5,879,319 A | 3/1999 | Pynson et al. |
| 5,882,327 A * | 3/1999 | Jacob ............................ 604/8 |
| 5,893,837 A | 4/1999 | Eagles et al. |
| 5,968,058 A | 10/1999 | Richter et al. |
| 6,007,511 A | 12/1999 | Prywes |
| 6,050,970 A | 4/2000 | Baerveldt |
| 6,077,299 A | 6/2000 | Adelberg et al. |
| 6,102,045 A | 8/2000 | Nordquist et al. |
| 6,142,969 A | 11/2000 | Nigam |
| 6,168,575 B1 | 1/2001 | Soltanpour |
| 6,280,449 B1 * | 8/2001 | Blake |
| 2002/0143284 A1 * | 10/2002 | Tu et al. ........................ 604/9 |

* cited by examiner

GLAUCOMA TREATMENT DEVICE AND METHOD

BACKGROUND

The invention relates to devices and methods for treating glaucoma.

Glaucoma is the leading cause of irreversible blindness in the world. It is estimated that 70 million people worldwide have glaucoma, and that nearly 7 million are bilaterally blind from this disease. In the United States, 2.5–3 million people suffer from glaucoma, and it is the third most common reason for adults to visit a medical doctor. Elevated intraocular pressure is the outstanding risk factor for the development of glaucoma, and the main reason for progression of the disease. Accordingly, treatment of glaucoma has been focused on lowering the intraocular pressure in the affected eye.

Glaucoma treatment has customarily comprised a three-step process. First, medicines are tried, such as beta-adrenergic antagonists and alpha-adrenergic agonists. These have proven only moderately, and inconsistently, effective, and can lead to many, sometimes life threatening, side effects, such as respiratory and cardiac side-effects. If medical treatment is either not effective or not tolerated, argon laser trabeculoplasty (ALT) is usually the next step. ALT success is often limited, and is ultimately temporary. The final therapeutic step involves surgery. Trabeculectomy is by far the most common type of surgery done for treatment of glaucoma. It was first described by Cairns in 1969, slightly modified by Watson 1969–71, and has changed little during the last three decades. In a trabeculectomy, a hole is made in the eye near the limbus and into the anterior chamber, under an overlying scleral flap. The aqueous humor thereby is allowed to drain into the subconjunctival space. Subsequent scarring circumscribes this area of subconjunctival drainage into a bleb. Sometimes, the scarring progresses to completely scar down the bleb, stopping the flow of aqueous humor, and causing the surgery to fail. Mitomycin C, an anti-fibroblastic drug, has been used to combat scarring attendant to trabeculoctomy. While increasing surgical success, however, the use of this drug has significantly added to the risks and complications of filtering surgery; mitomycin C causes thinning of the conjunctiva and can lead to leaking through the thinned conjunctiva, and such leaking often leads to hypotony and intraocular infection.

Glaucoma drainage devices (GDD) are an attempt to control the scarring which so commonly tends to seal conduits made in tissue. Molteno, in 1969, described the first of the currently used type of GDD. They consist of a tube and a plate made of synthetic biomaterials. The tube is inserted into the anterior chamber and conducts the aqueous humor to the plate, which is in the subconjunctival space. The problem remains, however, of scarring of the bleb which forms around the plate. About 80% of GDDs appear to be successful for one year, with a 10% additional failure rate each year thereafter. There are significant complications associated with these devices, both in the perioperative and postoperative periods, including hypotony, flat anterior chamber, suprachoroidal hemorrhage, retinal detachment, a hypertensive phase, endophthalmitis, diplopia, corneal decompensation, conjunctival melting, and others. One or more complications have been found to occur in 60–70% of cases.

SUMMARY

In one aspect, the invention features a device for treating glaucoma in an afflicted eye. The device includes a body defining a lumen, the body having first and second ends, and external and lumenal surfaces. The body has a length sufficient to provide fluid communication (i.e. the flow of aqueous humor) between the anterior chamber and tear film of the eye when the device is implanted in the sclera. The device further includes a filter capable of providing outflow resistance to aqueous humor flowing through the lumen.

In preferred embodiments, the second end of the device body is adapted to lie, and remain, substantially flush with the scleral surface when the device is implanted in the sclera. The device is preferably flared at the second end to aid in providing an endpoint for the depth of insertion of the device into the sclera.

The body of the device is preferably fabricated from a material selected from the group consisting of silicone, polypropylene, polymethyl methacrylate, and polytetrafluoroethylene.

In preferred embodiments, at least a portion of the external surface of the body is coated with a porous cellular ingrowth coating. Preferably, the porous cellular ingrowth coating is coated on the portion of the device that is in contact with the sclera when the device is implanted. The remaining surfaces of the device—the entire lumenal surface, the portion of the external surface not in contact with the sclera, and the filter surfaces of the device—are preferably coated with a bio-inert surface coating.

The filter is preferably a microporous filter membrane. In preferred embodiments, a filter membrane may be fused to the periphery of the body at the lumenal opening at the second end of the body to form a one-piece device for implantation in the sclera. The filter has an inflow face, an outflow face and a peripheral edge. Preferably the peripheral edge of the filter is contiguous with the body of the device, and more preferably is contiguous with the device body at the lumenal opening in the second end of the body. Alternatively, in other embodiments the device may be a unitary article in which a microporous filter membrane is integral with the material used to form the body of the device.

In preferred embodiments of the device, the microporous filter membrane may comprise a silicon(e) or silicon(e)-based microporous filter membrane, a microporous polymer network, a fiber network, or microcapsular material.

Preferably, micropores in the microporous filter membrane have a diameter less than or equal to about 0.2 microns.

The devices of the present invention have a length sufficient to provide fluid communication between the anterior chamber and tear film of the eye when the device is implanted in the sclera. Preferably, the devices have a length of at least about 2.5 mm.

The diameter of the lumen of the device is preferably about 0.5 mm or less. The diameter of the lumen may increase at the second end of the device in those embodiments where the second end of the device is flared.

In preferred embodiments of the devices of the present invention, at least a portion of the external surface of the body, preferably corresponding to the portion of the surface extending into the anterior chamber, all of the surface of the lumen, and the filter surfaces includes a bio-inert surface coating. The bio-inert surface coating may, for example, include phosphoryl choline or polyethylene oxide.

The device preferably may also include at least one barb, preferably extending from the external surface of the device body in the portion of the body in contact with the sclera when the device is implanted. The barb or barbs are adapted to engage with the sclera to provide stability when the device is implanted.

The device is preferably beveled at its first end to aid in the implantation process.

In another embodiment, the device includes, at its second end, a lip extending around at least a portion of the periphery of the second end, the lip having an external lip surface continuous with the external surface of the body. A portion of the external surface of the lip is adapted to contact the external scleral surface of the eye when the device is implanted in the sclera. Preferably, the lip includes a porous cellular ingrowth coating on at least a portion of its external surface, and the lip preferably extends around at least half the circumference of the second end of the device.

In still another embodiment, the second end of the device body includes a head portion having a cavity in communication with the lumen of the body, wherein the head portion has opposing inner and outer faces such that the inner face is in contact with the surface of the eye when the device is implanted, and the outer face includes the filter. The inner surface of the head portion may include a porous cellular ingrowth coating. Preferably, the filter is contiguous, at its peripheral edge, with the peripheral edge of the outer opposing face of the head portion that defines an opening in the cavity.

In another aspect, the invention features a one piece device for treating glaucoma in an afflicted eye. The device includes a body defining a lumen and having first and second ends. The body is of sufficient length to provide fluid communication between the anterior chamber and the tear film of the eye when the device is implanted in the sclera. The device further includes a filter having inflow and outflow faces, and a peripheral edge. At least a portion of the peripheral edge of the filter is contiguous with the body.

In still another aspect, the invention features a method for treating glaucoma in an afflicted eye. The method involves the steps of providing a device as disclosed herein, and implanting the device in the sclera of the eye such that aqueous humor flows from the anterior chamber to the tear film of the eye. In all embodiments of the method, the method involves the step of making an incision into the anterior chamber of the eye prior to implantation of the device. The method may further involve suturing the second end of the device to the sclera following implantation.

The details of one or more embodiments of the invention are set forth in the accompanying drawings and the description below. Other features, objects, and advantages of the invention will be apparent from the description and drawings, and from the claims.

DETAILED DESCRIPTION

The invention relates to novel devices and methods for treating glaucoma. In particular, the invention relates to devices wherein a generally tubular body is provided which is of sufficient length to allow aqueous humor to flow from the anterior chamber of an afflicted eye through a lumen of the tubular body and into the tear film when the device is implanted in the sclera. A filter capable of providing outflow resistance to aqueous humor flowing through the lumen is provided in the device. The device may be implanted in the sclera of an afflicted eye to treat glaucoma.

The devices of the invention provide numerous advantages. The devices drain aqueous humor into the tear film, rather than into the subconjuctival space. No conjunctival bleb is formed, and therefore there is no potential to scar. In preferred embodiments, a filter portion is fused or bonded to the body to form a one-piece device having a simple design and which is easy and safe to insert into an afflicted eye. The filter is readily accessible for vacuum or chemical cleaning. Aqueous humor is expelled into the tear film, enhancing moisture and lubrication in the eye. Also, in preferred embodiments, the filter is comprised of a microporous membrane material. The microporous membrane comprises pores sized to block all bacteria, and pore number and length may be calculated to provide aqueous humor outflow that yields desirable intraocular pressure. The materials used to make the device may be selected to provide bulk biocompatibility by both seeking to match scleral rigidity, and by providing the portion of the device that is in contact with eye tissue with a porous cellular ingrowth surface to promote biointegration. Both the scleral rigidity compatibility and the biointegration contribute to the elimination of micromotion of the device. The biointegration will also eliminate potential dead space around the device, thus removing the risk of a tunnel infection into the eye. The surfaces of the device may also be coated with other materials, such as polymer coatings or biologically active molecules, to promote surface biocompatibility and/or immobilization of the implanted device.

Figure 1A:
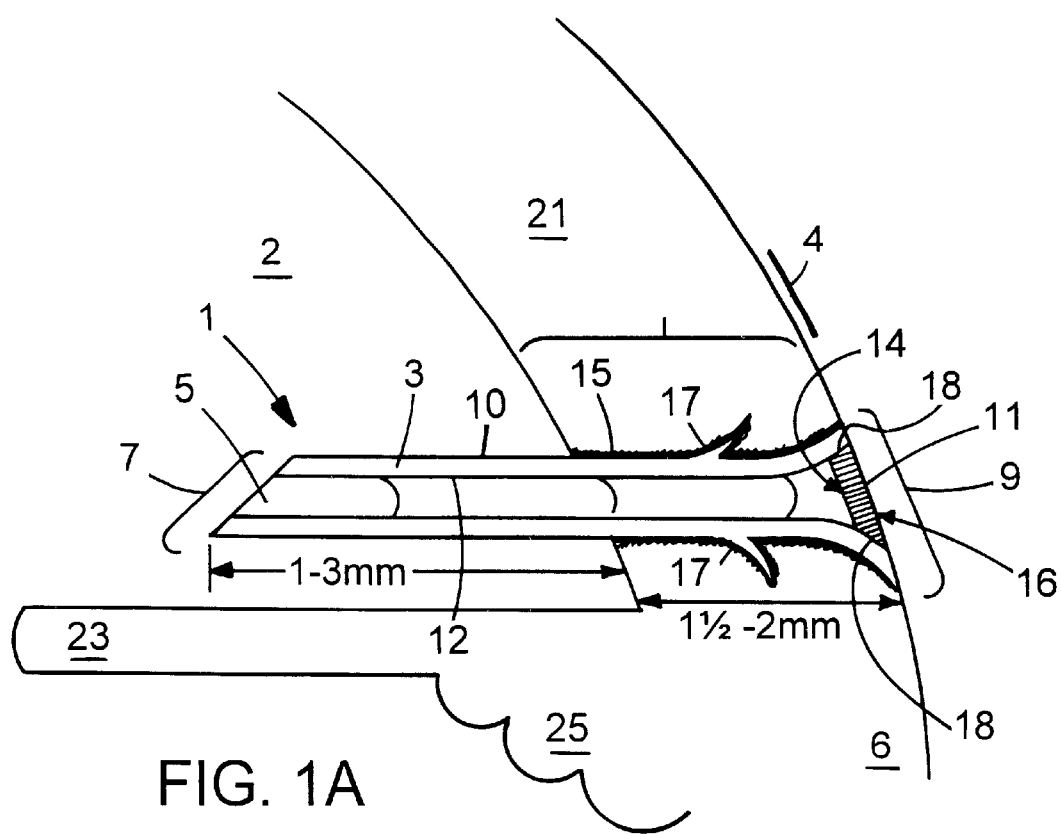
FIG. 1A is a mid-horizontal cross-sectional view of an eye with one embodiment of a device illustrative of the present invention implanted and shown in longitudinal cross section.
Figure 1B:
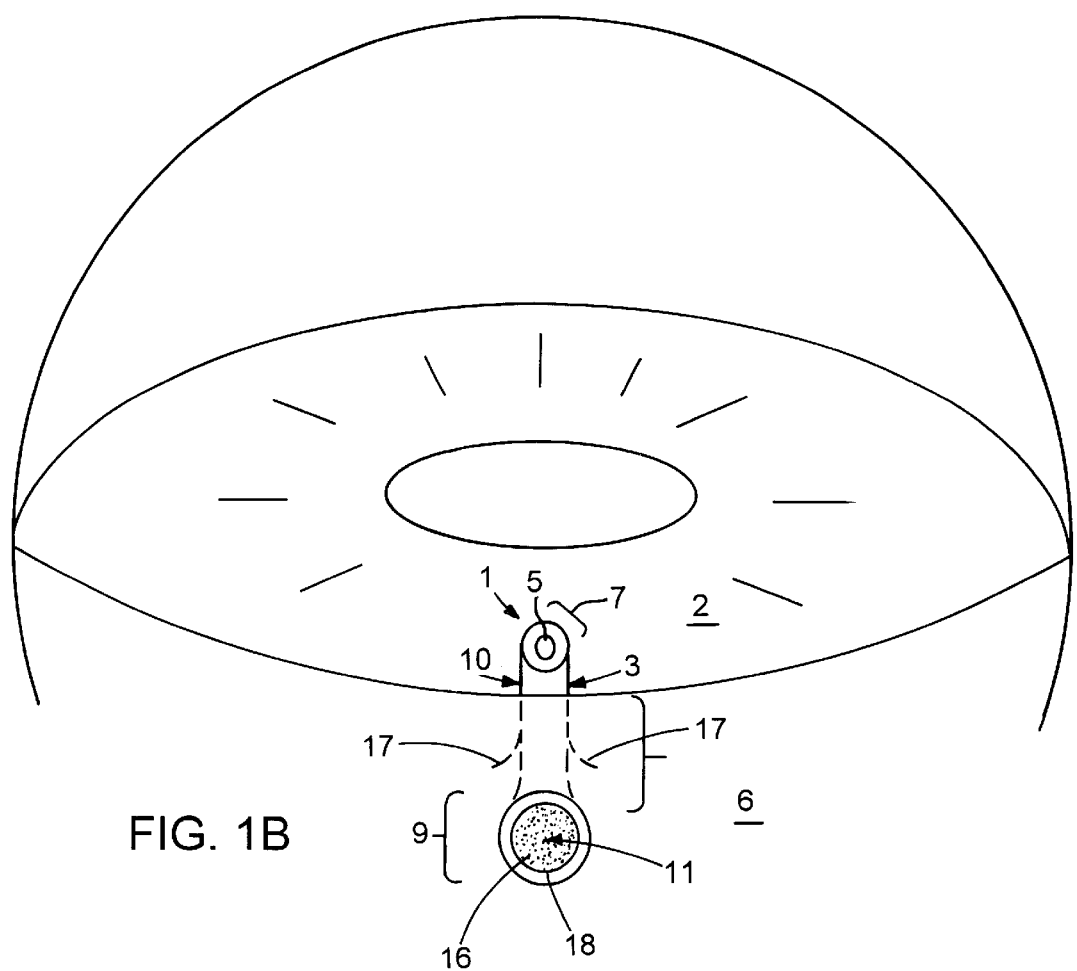
FIG. 1B is an external view of an eye showing the external, intrascleral, and intra-anterior chamber portions of the device shown in FIG. 1A implanted in an eye.

A device illustrative of one embodiment of the present invention is shown in FIGS. 1A and 1B. As shown in longitudinal cross-section in FIG. 1A as implanted in an eye, the device 1 includes a body 3 defining a lumen 5 and having a first end 7 and a second end 9. The body has an external surface 10, and a lumenal surface 12. A filter 11 is provided at the second end 9 of the device. The filter 11 has an inflow face 14, and outflow face 16, and a peripheral edge 18. The device has a length sufficient to provide fluid communication between the anterior chamber and tear film of an eye when the device is implanted in the sclera. The filter 11 is capable of providing outflow resistance to aqueous humor flowing through the lumen 5. The device 1 is implanted in the sclera 6 of the eye. Also shown in FIG. 1A are the cornea 21, the iris 23, and the ciliary body 25.

The body 3 of the device is preferably formed of a material selected from the group consisting of silicone, polypropylene, polymethyl methacrylate, and expanded polytetrafluoroethylene (preferably denucleated and coated with laminin). These materials are well known in the art and methods of fabricating tubular structures from such materials also are well-known. The material from which the device is fabricated is selected to provide bulk biocompatibility, as described above. The bulk properties of the material may be selected to impart rigidity as close as possible to that of the surrounding tissue, e.g. sclera.

In accordance with the invention, the device is of sufficient length to provide fluid communication between the anterior chamber 2 and tear film 4 when the device is implanted in the sclera 6 of an afflicted eye. In general, to provide fluid communication between the anterior chamber and tear film, the devices of this invention must have a minimum length of about 2 mm. In preferred embodiments, the device has a length of at least about 2.5 mm. In general, the device may have a length of between about 2.5 mm and about 5 mm. The preferred length of at least about 2.5 mm will reduce the possibility of blockage of the lumenal opening in the anterior chamber by the iris. The length of the device within the scleral tract would preferably be greater than the scleral thickness because insertion would not be perpendicular to the sclera, but more tangential to be parallel to the iris.

As shown in FIG. 1, the body 3 of the device defines a generally tubular lumen 5. In preferred embodiments, the lumen has a diameter less than or equal to about 0.5 mm. On its external surface 10, the body 3 may preferably include a porous cellular ingrowth coating 15 on at least a portion thereof. Preferably, and as shown in FIG. 1A, the portion of the external surface coated with the cellular ingrowth coating 15 corresponds substantially to the portion of the body in contact with eye tissue (i.e. sclera) following scleral implantation. Such porous cellular ingrowth coatings have been described with respect to other ophthalmic implants, and have been made of silicone with a reported thickness of 0.04 mm. Selected growth factors may be adsorbed on to this coating to enhance cellular ingrowth.

The remaining surfaces of the device—i.e. the entire lumenal surface 12, the portion of the external surface 10 not in contact with the sclera, and the inflow (14) and outflow (16) faces of the filter—may further include coatings to enhance surface biocompatibility. Such coatings may include bio-inert polymer coatings such as phosphoryl choline (PC) and polyethylene oxide (PEO), and such bio-inert surface coatings may be further modified with biologically active molecules such as heparin, spermine, surfactants, proteases or other enzymes, or other biocompatible chemicals amendable to surface immobilization. Both PC and PEO polymer coatings downregulate deleterious biological reactions, primarily by attracting a large and stable hydration shell when grafted onto a surface. PEO also is amendable to end-group coupling for surface immobilization of biologically active molecules, which might include heparin, spermine, surfactants, proteases (eg., papain) or other enzymes or chemicals. The addition of such bioactive molecules could advantageously impart specific desired functionality, for example, allowing a further increase in the hydrophilicity of the surface. Hydrophobic surfaced microporous filters are known to be much more prone to protein plugging than are microporous filters with hydrophilic surfaces.

In the portion of the external surface of the body 3 that is in contact with eye tissue following implantation, the body may include a barb or barbs 17 designed to engage with tissue upon implantation and provide stability to the implanted device. The barb or barbs 17 may be formed as part of the device body during manufacture or may be fused or bonded to the device body by suitable means known in the art. The device may also be beveled at its first end 7 to aid in the implantation process.

The devices of the invention include a filter capable of providing outflow resistance to aqueous humor flowing through the lumen of the device from the anterior chamber into the tear film. The filters employed in the devices of this invention preferably are microporous filter membranes.

In FIG. 1, a microporous filter membrane 11 is shown at the second end 9 of the body 3. The microporous filter membrane 11 includes inflow face 14, outflow face 16, and is circumscribed by peripheral edge 18. The size of the pores in the filter-membrane 11 at the exterior surface of the device preferably are approximately $0.2\mu$, or smaller. This is sufficiently small enough to prevent ingress of all known bacteria. It is also about the same pore size as has been shown to be present in the capsule formed around Molteno implant plates, and through which aqueous humor flows by simple, passive diffusion. That capsule is known to act as an "open sieve" for passage of latex microspheres of $0.2\mu$ and smaller. The filter-membrane of this device would be expected to act as such an "open sieve," but with a predetermined resistance to outflow to result in a low to normal intraocular pressure. The design parameters of microporous membranes suitable for use in the present invention may be summarized as follows.

Porous media theory allows the calculation of the resistance of a fluid through a porous structure by using the formula: resistance=8×fluid viscosity×length of pore/number of pores×π×pore radius to the fourth power. The viscosity of aqueous humor is essentially the same as saline, and the viscosity is stable. The pore radius could vary only over a range that would still permit it to act as a barrier to bacteria. The length of the pores, however, may be varied, and is determined by the thickness of the filter-membrane. The number of pores can also be varied to arrive at a desired resistance. Even though the eye's natural outflow is compromised in glaucoma, it is rarely zero, and would in most cases allow for a certain tolerance in the system even after the present device is in place. In fact, the main natural outflow of the eye, the conventional or trabecular meshwork pathway, is intraocular pressure dependent. The trabecular meshwork pathway serves as a one-way valve, so when the intraocular pressure is very low, the trabecular meshwork is compressed with very little outflow, or backflow, allowed through it. When the intraocular pressure increases, to a certain level, the outflow can increase also.

In preferred embodiments of the invention, it is desirable to achieve a normal aqueous humor outflow resistance of about 3.2 mmHg×min/$\mu$l. For example, if a filter membrane with a diameter of 1.0 mm is used, that would result in a filter membrane area of 785,000 square $\mu$. If a pore density of 40% of the filter membrane surface area is used, there would be ten $0.2\mu$ pores/square $\mu$. Thus, there would be a total of 7,850,000 pores of $0.2\mu$ size. Using a filter membrane thickness of $100\mu$, the porous membrane theory equation for resistance would be:

$R$=8×viscosity×pore length/pore number×π×pore radius to the fourth power=8×1×100/7,850,000×3.14×0.00001=800/247=3.2, the mean value for outflow resistance of normal, non-glaucomatous, eye.

Because episcleral venous pressure would not be a factor in the function of this device, as it is in the determination of normal intraocular pressure [eg., P(ocular)=F(inflow)/C (facility of outflow)+P(evp)], the IOP with this device might be expected to be below normal. Alternatively, the outflow through the device, rather than the outflow resistance, could be adjusted to give the desired intraocular pressure.

Microporous filter membranes that have been used with ophthalmic devices or research include Nuclepore polycarbonate filter membranes, millipore filters, and microperforated silicone membranes. However, filter-membrane nanotechnology may be useful to fabricate microporous membranes, in accordance with the invention, to be optimally biocompatible, non-degradable, and immunoisolating. Examples of such technologies that are known and characterized in the art include:

1) Microfabricated silicone-based biocapsules, an example of which would be polycrystalline silicone filter-membranes micromachined to present a high density of uniform pores, as small as 0.02 $\mu$.
2) Microporous polymer networks, an example of which would be a polyurethane network formed by cross-linking a mixture of linoleic acid and a linear poly (etherurethane) with dicumyl peroxide. Microporosity is introduced by adding salt crystals before cross-linking and leaching it out afterwards. Pore size in this instance is 0.3–0.7$\mu$, with a membrane thickness of 8$\mu$. But, both pore size and membrane thickness can be varied.
3) Fiber networks with a porous structure, an example of which would be an acrylonitrile membrane (AN 69).
4) Microcapsules based on the use of oligomers which participate in polyelectrolyte complexion reactions.

The application of these technologies to medicine has heretofore been most prominently related to pancreas cell transplantation.

In FIG. 1, the microporous filter membrane 11 is attached at its periphery 18 to the body 3 at the second end 9 of the body. The lumenal opening at the second end is thus closed by the microporous filter membrane. As shown in FIG. 1A, and in preferred embodiments of the invention, the filter 11 is bonded, fused or otherwise attached to the body at the second end of the device, most preferably at the edge of the second end defining the lumenal opening, such that the filter is substantially flush with the second end of the body. Although preferred, such placement of the filter is not required, the filter could be placed elsewhere, for example in a slightly recessed or protruding position. In an alternative embodiment of the device of this invention, the filter may be formed of the material used to fabricate the device body and be integral with it. In this alternative embodiment, manufacture of the device could occur as a one-step fabrication process to fabricate the tubular body which would be closed at one end (corresponding to the second end of the ultimate device) with body material of a desired thickness. A microporous filter membrane can then be fabricated at the closed end by creating a desired number of pores of appropriate diameter, by perforation or other suitable means. This device could then be implanted in the sclera in accordance with the present invention.

As shown in FIG. 1A, the fixation of the filter membrane, by fusion, bonding, or other means of attachment, results in a one-piece device that may be implanted as such in the sclera of an afflicted eye. The shape of the filter membrane may preferably be either round or oval.

As also shown in FIG. 1, the body 3 of the device flares at the second end 9, and the filter and second end 9 of the device are situated substantially flush with the external scleral surface 21. The flaring of the body at its second end 9 aids in the flush mounting of the device in the eye by providing an endpoint of insertion as the device is pushed into the sclera during surgery. The device 1 is also beveled at its first end 7 to assist in implantation. In this embodiment, the diameter of the filter membrane thus exceeds the diameter of the lumen in the portion of the body that is not flared. The degree to which the body flares and the resultant diameter of the microporous filter membrane may be adjusted to optimize the functional properties of the filter membrane. With the second end of the device, including the filter, in communication with the tear film, the filter is readily accessible for vacuum or chemical cleaning.

FIG. 1B depicts a device, as shown in FIG. 1A, implanted in an eye with like numbers signifying like features. The view shown in an external view of an eye showing the external, intrascleral, and intra-anterior chamber portions of the device shown in FIG. 1A implanted in the eye. A frontal view of the second end 9 and filter 11 (with outflow face 16 and peripheral edge 18 visible) is shown, and the device extends through the sclera 6 and into the anterior chamber 2. The flaring of the second end 9 of the device within the sclera is shown, and the second end is substantially flush with the scleral surface.

Figure 2A:
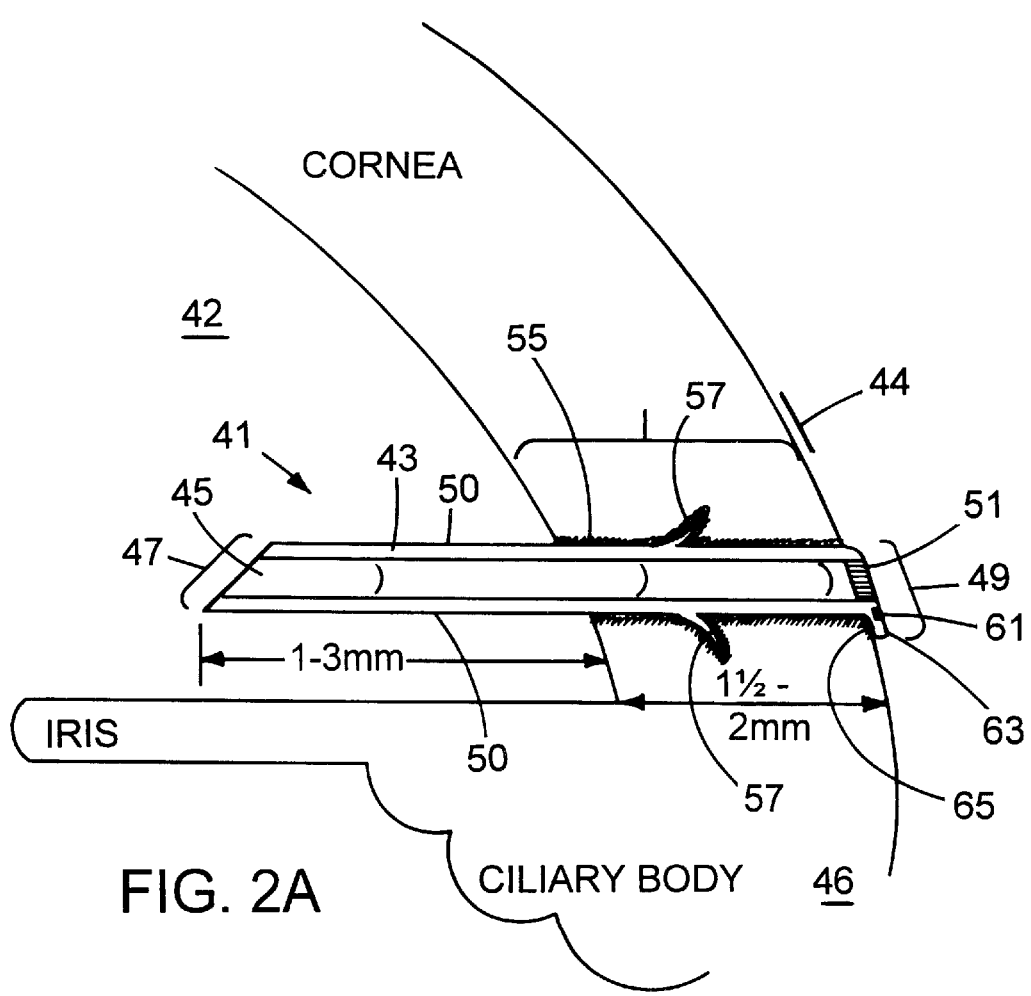
FIG. 2A is a mid-horizontal cross-sectional view of an eye with another embodiment of a device illustrative of the present invention implanted and shown in longitudinal cross section.
Figure 2B:
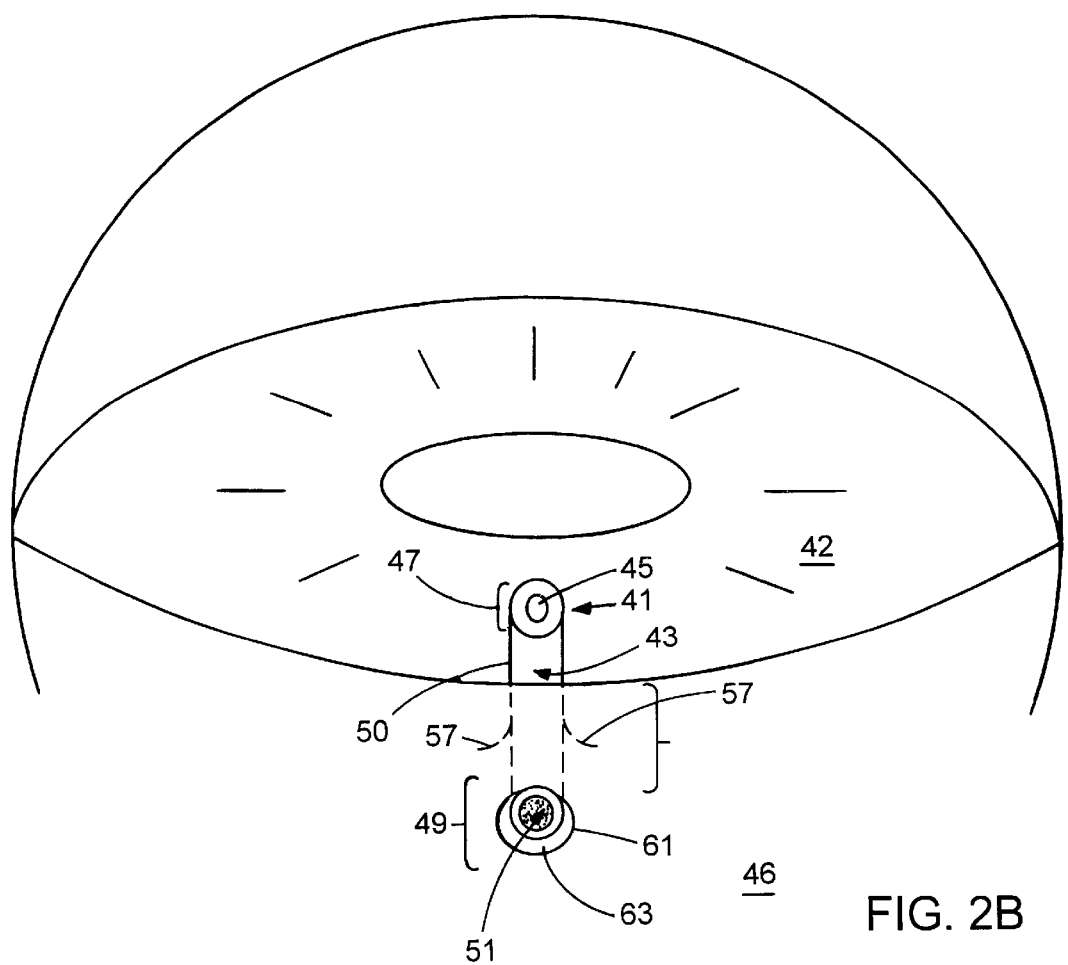
FIG. 2B is an external view of an eye showing the external, intrascleral, and intra-anterior chamber portions of the device shown in FIG. 2A implanted in an eye.

FIGS. 2A and 2B show another embodiment of the device of the present invention, with like numbers signifying like features. The views of the device embodiment shown in FIGS. 2A and 2B are similar to those shown in FIGS. 1A and 1B. The features of the devices shown in FIGS. 1A/1B and 2A/2B are similar in all respects except where noted. A device 41 is shown, having a body 43, a lumen 45, a first end 47, and a second end 49. Also shown are filter 51, porous cellular ingrowth coating 55, stabilization barbs 57, and a bevel at the first end 47. As with other embodiments, the device 41 is of sufficient length to allow fluid communication between the anterior chamber 42 and tear film 44 of an eye through the lumen 45 when implanted in the sclera 46.

In the embodiment shown in FIGS. 2A and 2B, the device comprises a head portion 61 which is not substantially flush with, but rather extends externally to the scleral surface. The body 43 of the device is adapted to form a lip 63 at the second end 49 of the device. The lip 63 extends around at least a portion of the filter 51 of the device (shown as extending for roughly ¾ of the circumference of the head portion 61). The lip 63 has an external lip surface 65 that is continuous with the external surface 50 of the body. The lip 63 serves to stabilize the device against the scleral surface, and the external lip surface 65 may be provided with porous cellular ingrowth coating 55 (as shown in FIG. 2A) to further stabilize the device in the eye. The lip 63 further provides an endpoint of insertion when the device is implanted.

Figure 3A:
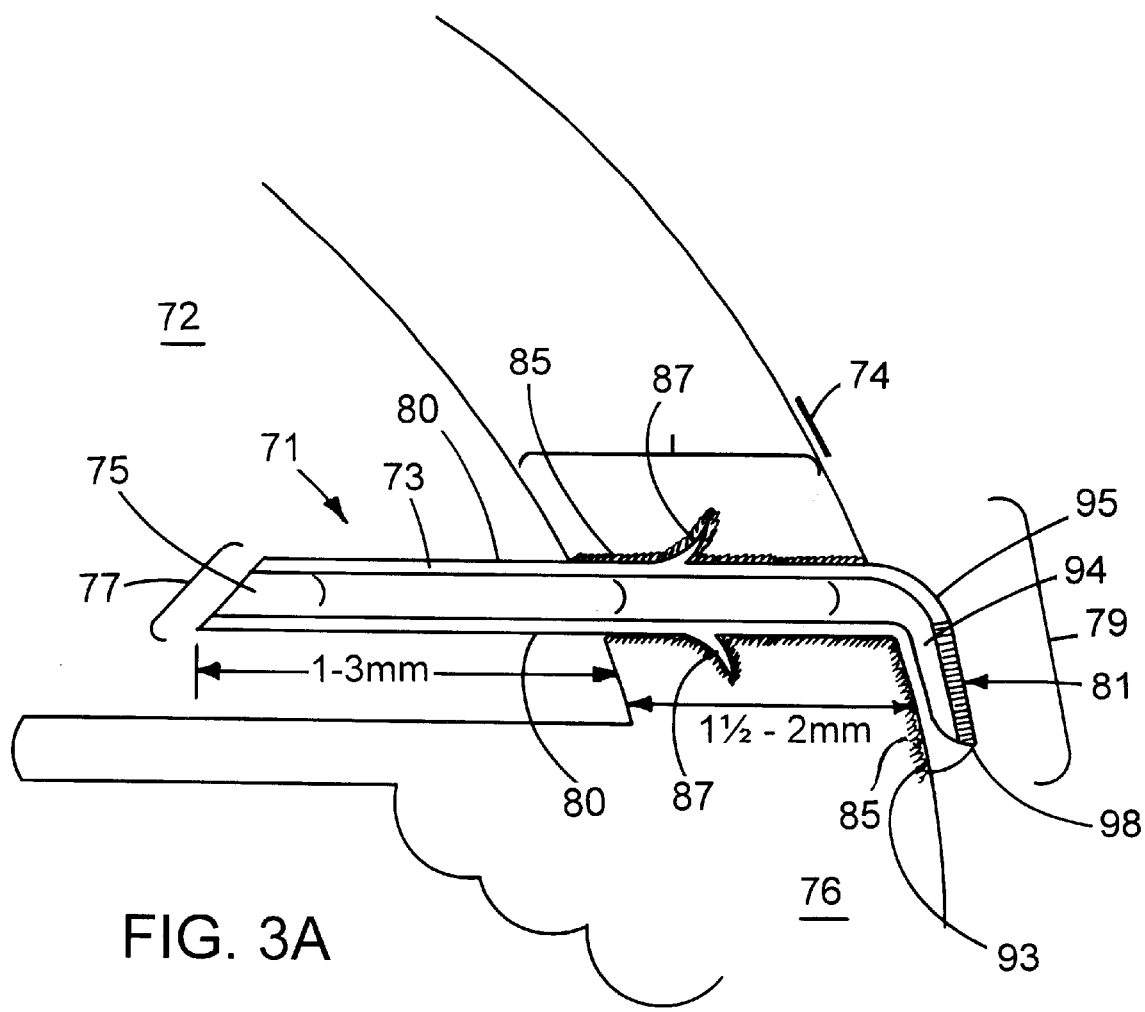
FIG. 3A is a mid-horizontal cross-sectional view of an eye with another embodiment of a device illustrative of the present invention implanted and shown in longitudinal cross section.
Figure 3B:
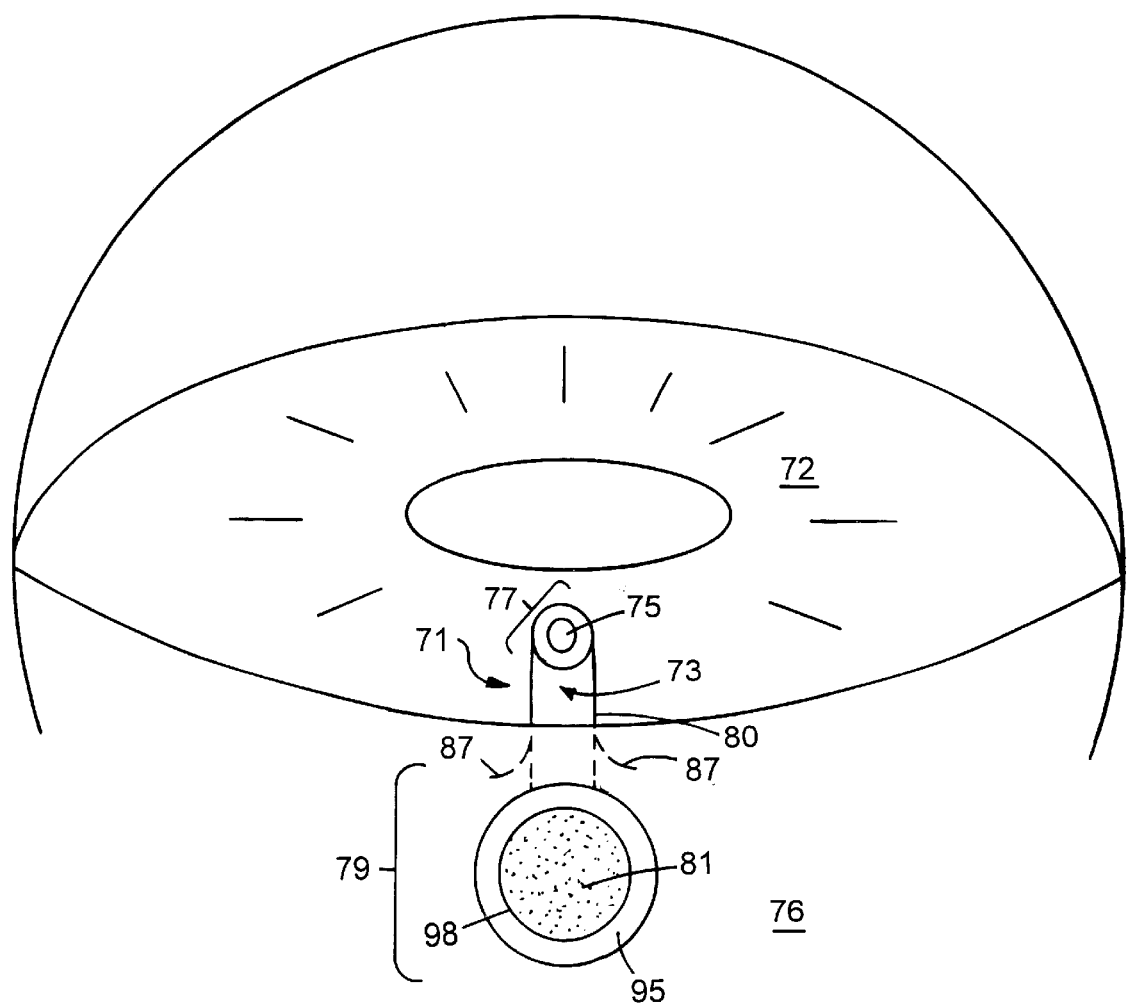
FIG. 3B is an external view of an eye showing the external, intrascleral, and intra-anterior chamber portions of the device shown in FIG. 3A implanted in an eye.

FIGS. 3A and 3B depict still another embodiment illustrative of the device of the invention, with like numbers signifying like features. The view of the device embodiment shown in FIGS. 3A and 3B are similar to those shown in FIGS. 1A and 1B. The features of the devices shown in FIGS. 1A/1B and 3A/3B are similar in all respects except where noted. A device 71 is shown, having a body 73, a lumen 75, a first end 77, and a second end 79. Also shown are filter 81, porous cellular ingrowth coating 85, stabilization barbs 87, and a bevel at the first end 77. The device is of sufficient length to allow fluid communication between the anterior chamber 72 and the tear film 74 when the device is implanted in the sclera 76.

In the embodiment shown in FIGS. 3A and 3B, the device comprises, at its second end 79, a disc-shaped head portion which is not flush with, but rather extends externally to the scleral surface. The body 73 of the device is adapted to form the disc portion, which includes a cavity 94 (FIG. 3A), which is in communication with the lumen 75. The disc-shaped head portion has opposing inner and outer faces 93 and 95, respectively. The inner face 93 (continuous with the external surface 80 of the body) is in contact with the external surface of the sclera 76, and the outer face 95 as shown in FIG. 3A includes the filter 81. The inner face 93 may be coated with porous cellular ingrowth coating 85. In preferred embodiments, a peripheral edge 98 of the filter 81 is contiguous with the periphery of the body 73 at the opening to the cavity 94, such that the filter 81 forms part of the outer face 95 of the disc-shaped head portion.

The method for installing this device is simple and consumes little time. Sometime before installation, topical antibiotic and non-steroidal anti-inflammatory drops (NSAID) should be applied to the operative eye. These will be continued for one week postoperatively four times a day. The NSAID helps stabilize the blood-aqueous barrier.

All embodiments of the device illustrated herein may be inserted under topical anesthesia, possibly supplemented subconjunctivally. In general, the devices of the invention may be inserted into the sclera using routine operative procedures. The location of insertion for all embodiments is in the sclera at about the posterior surgical limbus. The device could be inserted at any site around the limbus, but would preferably be inserted at the far temporal limbus.

The insertion procedure is begun by excising a small amount of conjunctiva at the site of the anticipated insertion, exposing the underlying sclera. Any bleeding is then cauterized. For embodiments of the device as shown in FIG. 2 and FIG. 3, a superficial layer of sclera may be excised beneath the anticipated position of the exterior portion of the device. This will allow these embodiments to be more flush with the surrounding external scleral surface, as occurs easily with the embodiment of FIG. 1.

Then, approximately 1–2 mm posterior to the limbus, at the site of the now exposed sclera, a diamond blade is used to make a stab incision into the anterior chamber, while held roughly parallel to the iris. This blade is of a size predetermined to make an opening into the anterior chamber sized appropriately for the introduction of the device. This stab incision is made gently, but relatively quickly, assiduously avoiding any and all intraocular structures. Such an uneventful paracentesis has been found not to disrupt the blood-aqueous barrier in most cases. In any event, any disruption of this barrier is usually of less than 24 hours duration without continued insult. In the embodiment of the device shown in FIG. 1, the paracentesis could be customized to the flared external shape of the device by using a diamond blade, or trochar, sized to the device, and fitted with a depth guard. This would insure accurate and predictable depth of insertion so the exterior surface of the device would lie flush with the external scleral surface.

The device is next picked up and held with a non-toothed forceps. The lips of the stab incision wound may be gaped with a fine, toothed forceps. The pointed tip of the tube element would then be gently pushed through the scleral tract of the stab incision and into the anterior chamber, with the tube lying above and parallel to the iris, with the bevel up [ie., anteriorly]. The flare in the embodiment of FIG. 1, the external lip in the embodiment of FIG. 2, and the disc portion in the embodiment of FIG. 3, provide for a definite endpoint to the depth of insertion. The embodiments of the device having a beveled first end, the bevel is oriented anteriorly so as to minimize the potential for blockage of the lumenal opening by the iris. The scleral barb(s) then stabilizes the device until the biointegration with the sclera is complete. This biointegration is a function of its porous cellular ingrowth surface, likely enhanced by adsorbed growth factors. In the embodiment of FIG. 3, a 10-0 nylon suture on a broad spatula needle may be used to suture the disc portion into the sclera, providing additional stability to the device until the biointegration is complete. This suture may then be easily removed. In the embodiments of FIGS. 1 and 2, a suture could also be used to add additional temporary stability.

After insertion of the device, an ocular shield should be placed over the eye.

Other embodiments of the invention are within the scope of the appended claims.

What is claimed is:

1. A device for treating glaucoma in an eye, comprising:
   a body defining a lumen and having first and second ends and external and lumenal surfaces, said body having a length sufficient to provide fluid communication between the anterior chamber and tear film of the eye through said lumen when said device is implanted in the sclera; and
   a filter membrane capable of providing outflow resistance to aqueous humor flowing through said lumen.

2. The device of claim 1, wherein second end of said device is adapted to lie substantially flush with the scleral surface when said device is implanted in the sclera.

3. The device of claim 2, wherein said body is flared at said second end.

4. The device of claim 1, wherein said body comprises a material selected from the group consisting of silicone, polypropylene, polymethyl methacrylate, and polytetrafluoroethylene.

5. The device of claim 1, wherein at least a portion of said external surface of said body comprises a porous cellular ingrowth coating.

6. The device of claim 5, wherein said portion of said external surface comprising porous cellular ingrowth coating corresponds to the portion of said external surface in contact with tissue when said device is implanted in the sclera.

7. The device of claim 1, wherein said filter comprises a microporous filter membrane.

8. The device of claim 7, wherein said microporous filter membrane comprises an inflow face, an outflow face, and a peripheral edge contiguous with said body.

9. The device of claim 7, wherein said microporous filter membrane comprises a silicon(e) or silicon(e)-based microporous filter membrane.

10. The device of claim 7, wherein said microporous filter membrane comprises a microporous polymer network.

11. The device of claim 7, wherein said microporous filter membrane comprises a fiber network.

12. The device of claim 1, wherein said body has a length of at least about 2.5 mm.

13. The device of claim 1, wherein said first end of said body is beveled.

14. The device of claim 1, wherein said lumen has a diameter of about 0.5 mm or less.

15. The device of claim 7, wherein said microporous filter membrane comprises micropores having a diameter less than or equal to about 0.2 microns.

16. The device of claim 1, wherein at least a portion of said external surface and of said lumenal surface comprises a bio-inert surface coating.

17. The device of claim 8, wherein said inflow and outflow faces comprise a bio-inert surface coating.

18. The device of claim 16, wherein said bio-inert surface coating is selected from the group consisting of phosphoryl choline and polyethylene oxide.

19. The device of claim 1, wherein said body comprises at least one barb, said barb adapted to engage with the sclera when said device is implanted in the eye.

20. The device of claim 1, wherein said filter is contiguous with the periphery of said second end of said body defining said lumen.

21. The device of claim 1, wherein said device comprises, at said second end, a lip extending around at least a portion of the periphery of said second end and having an external lip surface, wherein a portion of said external surface of said lip is adapted to contact the external scleral surface of said eye when said device is implanted in the sclera.

22. The device of claim 21, wherein at least a portion of said external surface of said lip comprises a porous cellular ingrowth coating.

23. The device of claim 21, wherein said lip extends around at least half of the circumference of said second end of said device.

24. The device of claim 1, wherein said second end of said body comprises a disc-shaped head portion, said disc-shaped portion having a cavity in communication with said lumen, said head portion comprising opposing inner and outer faces such that said inner face is in contact with the surface of said eye when said device is implanted and said outer face comprises said filter.

25. The device of claim 24, wherein said inner face of said head portion comprises a porous cellular ingrowth coating.

26. A one-piece device for treating glaucoma in an eye, comprising:

a body defining a lumen, said body having sufficient length to provide fluid communication between the anterior chamber and tear film of the eye when implanted in the sclera; and a filter membrane portion having an inflow face, an outflow face, and a peripheral edge wherein at least a portion of said peripheral edge is contiguous with said body defining said lumen.

27. The device of claim 26, wherein said filter is contiguous with the peripheral edge of said outer opposing face of said head portion.

28. A method for treating glaucoma, comprising:

providing a device, said device comprising a body defining a lumen and having first and second ends, said body having sufficient length to provide fluid communication between the anterior chamber and tear film of an eye, and said device comprising a filter membrane capable of providing outflow resistance to aqueous humor; and implanting said device in the sclera of the eye such that aqueous humor flows from the anterior chamber to the tear film of the eye.

29. The method of claim 28, comprising, prior to insertion of said device, making an incision into the anterior chamber of the eye.

30. The method of claim 28, comprising, following insertion of said device, suturing said second end of said device to the sclera.

31. The method of claim 28, wherein said device comprises at least one barb on its external surface positioned such that said barb is engaged with the sclera when said device is implanted in the eye.

32. The method of claim 28, wherein said device is flared at said second and said method further comprises implanting said device such that said second end is substantially flush with the surface of said eye.

33. The method of claim 28, wherein said device comprises, at said second end, a lip extending around at least a portion of the periphery of said second end, and wherein an inner surface of said lip is adapted to contact the external scleral surface of said eye when said device is implanted in the sclera.

34. The method of claim 28, wherein said second end of said body comprises a disc-shaped head portion, said disc-shaped portion having a cavity in communication with said lumen, said head portion comprising opposing inner and outer faces such that said inner face is in contact with the surface of said eye when said device is implanted and said outer face comprises said filter.

* * * * *

UNITED STATES PATENT AND TRADEMARK OFFICE
CERTIFICATE OF CORRECTION

PATENT NO.    : 6,595,945 B2
DATED         : July 22, 2003
INVENTOR(S)   : J. David Brown M.D.

It is certified that error appears in the above-identified patent and that said Letters Patent is hereby corrected as shown below:

<u>Column 12,</u>
Line 23, please insert -- end -- between "second" and "and".

Signed and Sealed this

Eleventh Day of November, 2003

JAMES E. ROGAN
*Director of the United States Patent and Trademark Office*